US007868211B2

(12) United States Patent
Rauls et al.

(10) Patent No.: US 7,868,211 B2
(45) Date of Patent: Jan. 11, 2011

(54) METHOD FOR THE PRODUCTION OF ENRICHED ISOPULEGOL

(75) Inventors: Matthias Rauls, Ludwigshafen (DE); Christoph Jaekel, Limburgerhof (DE); Nawid Kashani-Shirazi, Mannheim (DE); Klaus Ebel, Lampertheim (DE)

(73) Assignee: BASF SE, Ludwigshafen (DE)

( * ) Notice: Subject to any disclaimer, the term of this patent is extended or adjusted under 35 U.S.C. 154(b) by 87 days.

(21) Appl. No.: 12/064,731

(22) PCT Filed: Aug. 15, 2006

(86) PCT No.: PCT/EP2006/065322

§ 371 (c)(1),
(2), (4) Date: Feb. 25, 2008

(87) PCT Pub. No.: WO2007/023109

PCT Pub. Date: Mar. 1, 2007

(65) Prior Publication Data

US 2008/0214877 A1 Sep. 4, 2008

(30) Foreign Application Priority Data

Aug. 26, 2005 (DE) ........................ 10 2005 040 655

(51) Int. Cl.
C07C 35/08 (2006.01)
C07C 35/12 (2006.01)

(52) U.S. Cl. .................. 568/828; 568/829; 568/830

(58) Field of Classification Search ................. 568/828
See application file for complete search history.

(56) References Cited

U.S. PATENT DOCUMENTS

| 3,023,253 | A | | 2/1962 | Bain et al. |
| 3,064,311 | A | | 11/1962 | Bain et al. |
| 3,218,361 | A | * | 11/1965 | Webb ........................ 568/828 |
| 3,739,035 | A | | 6/1973 | Webb et al. |
| 5,447,541 | A | * | 9/1995 | Steiner et al. ................. 23/296 |
| 5,663,460 | A | | 9/1997 | Yamamoto et al. |
| 5,773,410 | A | * | 6/1998 | Yamamoto .................... 512/23 |
| 5,814,231 | A | | 9/1998 | Borho et al. |
| 5,914,012 | A | | 6/1999 | Kaibel et al. |
| 6,774,269 | B2 | | 8/2004 | Iwata et al. |
| 6,852,881 | B2 | * | 2/2005 | De Decker et al. .......... 562/600 |
| 2005/0169987 | A1 | | 8/2005 | Korber |
| 2006/0013748 | A1 | * | 1/2006 | Nordhoff et al. ............ 422/188 |
| 2008/0139852 | A1 | | 6/2008 | Bergner et al. |
| 2008/0167504 | A1 | | 7/2008 | Friedrich et al. |
| 2008/0207957 | A1 | | 8/2008 | Friedrich et al. |

FOREIGN PATENT DOCUMENTS

| CH | 350461 A | 1/1961 |
| DE | 2530481 A1 | 1/1977 |
| DE | 2534558 A1 | 2/1977 |
| DE | 3302525 A1 | 7/1984 |
| DE | 19536827 A1 | 4/1997 |
| DE | 10224087 A1 | 12/2003 |
| EP | 0804951 A2 | 11/1997 |
| EP | 1053974 A1 | 11/2000 |
| EP | 1225163 A2 | 7/2002 |
| FR | 1374732 | 10/1964 |
| JP | 2004121903 A | 4/2004 |
| WO | WO-03/083028 A2 | 10/2003 |
| WO | WO-2006/056435 A1 | 6/2006 |
| WO | WO-2006/069659 A1 | 7/2006 |
| WO | WO-2006/092433 A1 | 9/2006 |

OTHER PUBLICATIONS

Robert T. Morris & Robet N. Boyd, Organic Chemistry (5th ed., 1987).*
JJP van der Eerden and OSL Bruinsma, Science and Technology of Crystal Growth (Springer, 1995).*
Feteceau et al., 108 ACTA Mech., 225-231 (1995).*
Wynn, Nicholas P., "Separate Organics by Melt Crystallization", Chemical Engineering Progress, vol. 88, No. 3, (1992), pp. 52-60.
Wright, Fred, E., "The crystallization of menthol", J. Am. Chem. Soc., vol. 39, No. 8, pp. 1515-1525 (1917).
Kuhnert-Brandstaetter, et al. "Thermoanalytische Untersuchungen an Mentholen", Archiv der Pharmazie, vol. 307, No. 7, pp. 497-503 (1974).
Bernstein J., "Polymorphism in Molecular Crystals", Oxford, Clarendon Press, 2002, pp. 94-150 (2002).
Van't Land, C., M., "Industrial Crystallization of Melts", Marcel Dekker, pp. 61-63 (2005).
Arkenbout, G., F., "Melt Crystallization Technology", Technomic Publishing Company, Inc., Lancaster, Basel, pp. 229-232 (1995).

* cited by examiner

*Primary Examiner*—Brian J Davis
(74) *Attorney, Agent, or Firm*—Connolly Bove Lodge & Hutz LLP

(57) ABSTRACT

The present invention relates to a process for preparing enriched isopulegol by crystallization from a melt comprising isopulegol. The invention relates specifically to a process for preparing enantiomerically enriched n-isopulegol proceeding from optically active isopulegol having a relatively low enantiomeric excess by crystallization from the melt. The invention further relates to a process for preparing menthol proceeding from enantiomerically and/or diastereomerically enriched n-isopulegol prepared by crystallization from the melt.

14 Claims, No Drawings

METHOD FOR THE PRODUCTION OF ENRICHED ISOPULEGOL

RELATED APPLICATIONS

This application is a national stage application (under 35 U.S.C. §371) of PCT/EP2006/065322, filed Aug. 15, 2006, which claims benefit of German application 10 2005 040 655.6, filed Aug. 26, 2005.

TECHNICAL FIELD OF THE INVENTION

The present invention relates to a process for preparing enriched isopulegol by crystallization from a melt comprising isopulegol. The invention relates specifically to a process for preparing enantiomerically enriched n-isopulegol proceeding from optically active isopulegol having a relatively low enantiomeric excess by crystallization from the melt. The invention further relates to a process for preparing menthol proceeding from enantiomerically and/or diastereomerically enriched n-isopulegol prepared by crystallization from the melt.

Menthol is a naturally occurring active ingredient which finds wide use in pharmacy, cosmetics and the food industry. In natural sources, for example peppermint oil, menthol occurs in the form of four diastereomeric enantiomer pairs, of which only the main component, (−)-menthol, has the desired taste and other sensory properties. A multistage purification of natural menthol is therefore always unavoidable. When menthol is obtained synthetically, it has to be ensured by the synthesis route that the end product is pure (−)-menthol. Since this is generally possible only incompletely, if at all, the reaction products have to be separated from one another by process technology methods here too. The further diastereomers present in addition to (−)- and (+)-menthol can, though with considerable cost and inconvenience, be removed by distillation. (−)- and (+)-menthol, in contrast, owing to their identical physical properties, cannot be separated in this way.

Processes for separating optical isomers, in general or specifically (+)- and (−)-menthol, are known in large numbers. The significant method groups are: a) direct crystallization of the active ingredient from a solvent or from the melt, b) formation of a diastereomeric derivative with a chiral agent (for example in the form of a salt or ester) and crystallization or distillation of the diastereomer mixture formed, which now differs in its physical properties, c) chromatographic methods and d) enzymatic methods. In addition, there exist laboratory methods which should, if anything, be referred to as experimental, but they are of no significance for an industrial application. A comprehensive review of all relevant methods and their various embodiments can be found, for example, in Jaques, J. et al., Enantiomers, Racemates and Resolutions, Krieger Publishing Co. 1994.

The extremely difficult direct crystal formation of menthol has been investigated many times. It has been known for some time that menthol crystallizes in several polymorphs which can be interconverted close to the melting point (see K. Schaum, Lieb. Ann. Chem. 308 (1899), p. 37). The polymorphs described form, depending on the temperature, an extremely complex phase system with isotrimorphic mixed crystal formation, as described by Kuhnert-Brandstatter et al. in Archiv der Pharmazie 307 (1974) p. 497. This unusual behavior leads to substantial mutual miscibility of the isomers in the solid state, so-called solid solutions, which usually prevents separation of the isomers by direct crystallization.

STATE OF THE ART

A solvent-free crystallization of menthol from the melt at very low temperatures (−60° C.) is described in WO 03/083028. In this case, menthol is isolated from an oil which is obtained from natural sources and comprises a multitude of further components.

A comparable process for isolating menthol from an essential oil by crystallization at temperatures down to −35° C. is described by S. Tandon et al. in Journal of Medicinal and Aromatic Plant Sciences, 20, (1998) 25-27.

DE 195 36 827-A relates to a process for separating liquid eutectic mixtures by crystallization on cooling surfaces to which seed crystals are applied, on which individual types of crystals grow and are removed in liquid form after heating of the surfaces.

Synthetic menthol is usually obtained via the intermediate stage of isopulegol, which differs from menthol only by a double bond in the isopropyl side chain. Menthol is released therefrom by hydrogenation without loss of stereospecificity. A process for accomplishing the isomer separation of menthol by crystallization, which is achievable only with difficulty, is disclosed in FR 1,374,732: there, the purification of isopulegol by fractional crystallization from petroleum ether or acetone at temperatures between −40° C. and −75° C. is described. This achieves separation of the isopulegol from its three further diastereomers.

U.S. Pat. No. 5,663,460 discloses the purification of (−)-n-isopulegol by crystallization from petroleum ether or advantageously from acetone at temperatures of from −20° C. to −60° C. This can also achieve a rise in the optical purity.

OBJECT OF THE INVENTION

Proceeding from the prior art, it is an object of the invention to provide a process which allows isopulegol to be provided in high chemical and optical purity and is suitable for economically viable use on the industrial scale. With regard to the use of the isopulegol to be prepared or its conversion products in humans, physiologically unsafe reagents or organic solvents shall be substantially dispensed with.

DESCRIPTION OF THE INVENTION AND OF THE PREFERRED EMBODIMENTS

The object is achieved in accordance with the invention by the provision of a process for preparing enriched isopulegol of the formula (I)

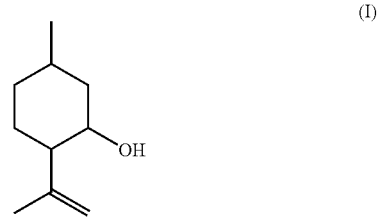

(I)

by crystallization from a melt comprising isopulegol of the formula (I).

The present invention accordingly relates to a process for purifying isopulegol by crystallization from a melt which, in addition to isopulegol, also comprises other undesired impurities or compounds, for example by-products which have occurred in the preparation of the isopulegol used, but is essentially free of solvents.

In the context of the present invention, the term "enriched isopulegol" is understood to mean one which has a chemical purity of at least about 90% by weight, preferably at least about 95% by weight and more preferably from about 95 to about 99.95% by weight. Isopulegol of the formula (I) is understood to mean a mixture of the four possible diastereomers of isopulegol, namely n-isopulegol, iso-isopulegol, neo-isopulegol and neoiso-isopulegol.

Suitable starting materials for performing the process according to the invention are isopulegol of any origin, i.e. isopulegol isolated from natural sources or synthetic isopulegol. The melt to be used in accordance with the invention consists of isopulegol preferably to an extent of at least about 70% by weight, more preferably to an extent of at least about 75% by weight, even more preferably to an extent of from about 80 to about 100% by weight and especially preferably to an extent of about 85 to about 100% by weight.

The invention relates specifically to a process for preparing enantiomerically and/or diastereomerically enriched n-isopulegol of the formula (II)

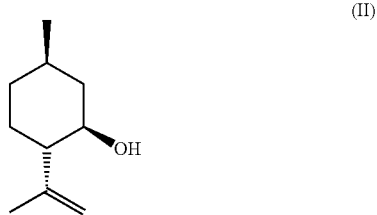

(II)

by crystallization from a melt comprising n-isopulegol of the formula (II), with or without further diastereomers of isopulegol.

Preferred starting materials or melts thereof consist of n-isopulegol of the formula (II) to an extent of at least about 70% by weight, more preferably to an extent of at least about 75% by weight and more preferably to an extent of from about 80 to about 100% by weight and most preferably from about 85 to about 100% by weight. Such melts may also comprise the aforementioned diastereomers of isopulegol in variable proportions and to a variable degree according to the origin and type of preparation of the n-isopulegol to be converted in accordance with the invention.

The n-isopulegol of the formula (II) obtainable from the melt by the inventive crystallization is typically obtained in diastereomerically enriched form. The term "diastereomerically enriched" should be understood to mean that the products obtainable in accordance with the invention have a higher content of the desired n-isopulegol diastereomer relative to the other aforementioned diastereomers than the melt used in accordance with the invention.

In the case of use of optically active starting materials, i.e. starting materials in which the two enantiomers of n-isopulegol are not present in the same ratio, enantiomerically enriched n-isopulegol is obtained in the crystallization process according to the invention. The term "enantiomerically enriched" should be understood to mean that the products obtainable in accordance with the invention have a higher content of one enantiomer of n-isopulegol relative to the other enantiomer, i.e. a higher enantiomeric excess (ee) than the melt used in accordance with the invention.

The process according to the invention accordingly also enables the preparation of enantiomerically and diastereomerically enriched n-isopulegol by crystallization from a melt comprising optically active n-isopulegol with a relatively low enantiomeric excess.

Starting materials preferred in accordance with the invention or melts thereof comprise n-isopulegol with an enantiomeric excess of at least about 75% ee, more preferably of at least about 80% ee and most preferably of from about 85 to about 90% ee.

In the case of use as described above of optically active starting materials, in the process according to the invention, what is obtained is typically n-isopulegol with an enantiomeric excess of at least about 85% ee, preferably from about 90 to about 100% ee, more preferably from about 95 to about 99.9% ee and most preferably from about 97 to about 99.9% ee.

The crystallization process according to the invention is suitable, in a preferred embodiment, for preparing enantiomerically enriched L-(−)-n-isopulegol of the formula (II*)

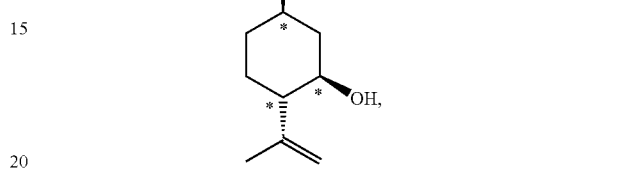

where * in each case denotes an asymmetric carbon atom in the absolute configuration shown, by crystallization of melts comprising L-(−)-n-isopulegol.

The term "crystallization from the melt" or "melt crystallization" is known to those skilled in the art and is described in detail, for example, in G. F. Arkenbout, Melt Crystallization Technology, Lancaster/Pa., Technomic Publ. Co., 1995. In the context of the present invention, this should be understood to mean a crystallization which is performed from the melt, i.e. from a mixture of liquid, i.e. molten and possibly already solidified, starting material without addition of further components, for example solvents or other assistants.

The inventive melt crystallization can be performed in the form of a layer crystallization or in the form of a suspension crystallization. To perform a layer crystallization, a cooled surface is typically introduced into the melt of the optically active or inactive isopulegol used as the starting material. Thereafter, a crystal layer of enantiomerically and/or diastereomerically enriched or unenriched isopulegol forms on the cooled surface introduced and can then be separated from the remaining mother melt. The crystalline enriched isopulegol thus obtained can be melted again in further assistant-free purification steps (for example by washing with pure product, "sweating" just below the melting point). Subsequently, this operation can be repeated as often as desired to increase the purity and the yield in the molten crystals and in the mother melt. Generally, in the context of layer crystallization processes to be performed advantageously in accordance with the invention, dynamic processes should be distinguished from static processes. In the dynamic processes, the mother phase, i.e. the molten starting material, is moved actively or passively along the crystals or the cooling surface. In the static processes, the inventive melt crystallization is performed in a standing melt.

The process according to the invention can accordingly also be performed in the form of a dynamic layer crystallization. In a preferred embodiment, this variant is performed in tube bundle heat exchangers as described in G. F. Arkenbout, Melt Crystallization Technology, Lancaster/Pa., Technomic Publ. Co., 1995 (chap. 6.2). In this method, melt and coolant, for example in the form of a trickle film, are conducted along the inner and outer walls of the heat exchangers. Such an apparatus allows easier removal of the crystalline isopulegol obtained from the mother melt and any sweating fractions obtained by simple efflux under the action of gravity and, apart from a circulation pump, does not require any further stirrer units.

To perform a dynamic layer crystallization, the optically active or inactive isopulegol which serves as the starting substance, typically with a temperature which is above its melting point and can be read off from the melt diagram, is introduced into the melt crystallizer as described above and conducted through the cooled tube bundle heat exchanger by pumped circulation. To achieve an advantageous crystallization result, the lowering of the cold carrier temperature is preferably selected such that a crystal layer of thickness from about 1 mm to about 50 mm, preferably from about 5 mm to about 20 mm, forms within a period of from about 0.5 h to about 10 h, preferably within from about 1 h to about 4 h. The coolant temperatures required for this purpose are generally from about 1 K to about 40 K, preferably from about 5 K to about 20 K, below the particular melting point.

After the dynamic layer crystallization has been performed, the remaining mother melt is typically discharged. By raising the temperature of the heating or cooling medium of the heat exchanger, it is possible to melt any adhering mother melt residues or any included impurities or to remove them by drainage. Advantageous heat carrier temperatures are in the range from about 15° C. to about 60° C., particularly advantageously from about 20 to about 30° C. In this process referred to as "sweating", according to the purity requirements, from about 1 to about 50% by weight, often from about 5 to about 20% by weight, of the crystallized isopulegol can be melted again. Finally, the remaining enantiomerically or diastereomerically enriched crystal layer is advantageously melted off and either sent to its further use or crystallized once again for further purification or increase in the enantiomeric or diastereomeric excess. The mother melt removed as described and the fraction released by sweating can be recycled into the process according to the invention to increase the yield. Alternatively, the possibility exists, before the "sweating" of the crystal layer, of washing it by contacting with molten pure product, i.e. freeing it of any firmly adhering mother liquor.

Alternatively, the inventive melt crystallization can also be performed in the form of a suspension crystallization. In this case, the crystals are typically obtained in suspended form in their mother melt without any need for a crystal layer to form. A continuous method at constant temperature and a discontinuous method with gradually lowered temperature are possible. Useful cooling surfaces here are, for example, walls of a stirred vessel which are equipped with a close-clearance stirrer, so-called scratching coolers or the wiped surfaces in a cooling disk crystallizer. Alternatively, the melt can also be cooled by applying a vacuum and adiabatic evaporation of the substance of value (or, less preferably, of a solvent added as an auxiliary). The suspended crystals can then be removed in a manner known to those skilled in the art, for example with any filter unit, for example a suction filter a centrifuge or a belt filter. Owing to the extremely high purifying action achievable in principle, the removal can also be effected by means of a scrubbing column, in which case the suspension of pure product melted at the bottom which has been conducted from the top toward a filter is conducted in the opposite direction as a scrubbing medium.

The inventive crystallization of isopulegol or n-isopulegol from the melt is performed advantageously at temperatures in the range from about −20° C. to about 15° C., preferably in the range from about −10° C. to about 15° C. and more preferably in the range from about −5° C. to about 14° C. The exact position of the temperature range depends solely on the optical and chemical starting purity of the starting material and the desired yield and can be read off from the melt diagram of the isopulegol used in the particular case by the person skilled in the art.

In the case of the preparation process according to the invention for enriched, preferably enantiomerically or diastereomerically enriched, isopulegol, it is possible to use all methods mentioned with good success. In a preferred embodiment of the process according to the invention, the crystallization is performed in a static layer crystallizer with internal heat exchanger surfaces. No particular requirements are made on the arrangement of the heat exchanger surfaces mentioned. Typically, the isopulegol used as the starting substance is introduced into the melt crystallizer with a temperature which can be read off from the melt diagram and is above its melting point, and the contents of the crystallizer are cooled, according to the purity of the starting material, to temperatures of from about −20° C. to about 15° C., preferably from about −10° C. to about 15° C., within a period of from about 5 h to about 30 h, preferably from about 10 to about 20 h. To achieve an advantageous crystallization result, preference is given to selecting cooling rates of from about 0.1 K/h to about 20 K/h, more preferably from about 0.5 K/h to about 5 K/h.

After crystallization of the desired amount of starting material, the remaining mother melt is advantageously discharged. By slowly raising the temperature of the heating/cooling medium of the heat exchanger, it is possible to melt any adhering mother melt residues or any incorporated impurities or to remove them by drainage. Advantageous heating rates are in the range between about 0.1 and about 20 K/h, preferably in the range from about 0.5 to about 5 K/h. In this process, which is referred to as "sweating", according to the purity requirements, from about 3 to about 60% by weight, often from about 10 to about 30% by weight, of the crystallized isopulegol can be melted again. Finally, the enantiomerically enriched crystal layer remaining can advantageously be melted off and either sent to its further use or crystallized once again for further purification or increase in the enantiomeric excess. The mother melt removed as described and the fraction released by sweating can be recycled into the process according to the invention to increase the yield.

In a further preferred embodiment of the process according to the invention, a dynamic suspension crystallization of optically active or inactive isopulegol can also be performed. To this end, a suspension crystallization as described above is performed in a suitable stirred crystallization reactor, for example one equipped with a close-clearance stirrer, or, for example, in a cooling disk crystallizer equipped with wiped cooling surfaces. This suspension crystallization can be effected either batchwise or continuously. To perform a batchwise suspension crystallization, the optically active or inactive isopulegol which serves as the starting substance is introduced into the melt crystallizer with a temperature which can be read off from the melt diagram and is above its melting point, and the contents of the crystallizer are cooled, according to the purity of the starting material, to temperatures of from about −20° C. to about 15° C., preferably from about −10° C. to about 15° C., within a period of from about 0.5 h to about 12 h, preferably from about 2 to about 6 h. To achieve an advantageous crystallization result, preference is given to selecting cooling rates of from about 0.1 K/h to about 20 k/h, more preferably from about 2 K/h to about 10K/h.

To perform a batchwise suspension crystallization, the optically active isopulegol which serves as the starting substance is typically introduced into a melt crystallizer as described above with a temperature which can be read off from the melt diagram and is above its melting point, and cooled, according to the particular purity of the starting material and the desired yield, to the temperature which can be read off from the melt diagram. At this constant temperature, fresh starting material is typically supplied to the crystallizer continuously or in individual portions, while an equally large amount of crystal-containing suspension is drawn off from the crystallizer continuously or in portions. To achieve an advantageous crystallization result, the size of the crystallizer is preferably selected such that a residence time of the crystals of from about 0.5 h to about 12 h, more preferably from about 2 h to about 6 h, is established.

The process according to the invention opens up an economically particularly advantageous route to enantiomerically or diastereomerically enriched isopulegol proceeding from isopulegol with lower enantiomeric or diastereomeric purity. At the same time, the process can be performed under very simple apparatus or process technology conditions and at technically and economically very efficiently realizable temperatures in only one process stage. The process according to the invention is performed in the absence of organic solvents and without addition of further assistants or components, for example crystallization seeds. No derivatizations of the starting compound to be purified with regard to its enantiomeric excess are needed.

As mentioned at the outset, isopulegol or isomers thereof are important intermediates for preparing menthol or isomers thereof. Menthol can be obtained from isopulegol by methods of hydrogenation known to those skilled in the art, specifically of catalytic hydrogenation over suitable transition metal catalysts, as described, for example, in Pickard et al., J. Chem. Soc. 1920, 1253; Ohloff et al., Chem. Ber. 1962, 95, 1400; Pavia et al., Bull. Soc. Chim. Fr. 1981, 24, Otsuka et al., Synthesis 1991, 665 or in EP 1 053 974 A. In the case of suitable selection of the reaction conditions, the relative or absolute configuration of the isopulegol used is preserved substantially, and in many cases completely. The enantiomerically or diastereomerically enriched isopulegol obtainable in accordance with the invention thus constitutes an attractive starting material for preparing enantiomerically or diastereomerically enriched menthol.

The present invention accordingly also relates to a process for preparing menthol, comprising the steps of a) preparing enantiomerically and/or diastereomerically enriched n-isopulegol of the formula (II) or (II*) by crystallization from a melt comprising n-isopulegol of the formula (II) or (II*) and if appropriate further diastereomers of isopulegol as described above and b) hydrogenating the enantiomerically and/or diastereomerically enriched n-isopulegol obtained in step a).

In a preferred embodiment, the process is suitable for preparing L-(−)-menthol proceeding from L-(−)-isopulegol. The latter is obtainable in various ways known to those skilled in the art, for example by cyclizing oxo-ene reaction of optically active citronellal in the presence of tris(2,6-diarylphenoxy) aluminum catalysts, as described, for example, in EP A-1 225 163.

In this context, it is especially remarkable that the purification or enhancement of the enantiomeric excess of menthol by crystallization constitutes a problem which, to date, has been solved only in a technically inadequate manner. In view of the marked chemical and steric similarity of isopulegol and menthol, it should be considered to be surprising that the inventive melt crystallization of isopulegol cannot be achieved with the same disadvantageous mixed crystal formation as in the case of menthol.

The examples which follow serve to illustrate the invention without restricting it in any way:

EXAMPLES

Example 1

Static Layer Crystallization of an Isopulegol Melt

A jacketed glass tube as a crystallizer was initially charged with 205 g of isopulegol of composition 95% (−)-n-isopulegol and 5% (+)-n-isopulegol (90% ee) with a melting point of 13° C. at a temperature of 15° C. The crystallizer was cooled down to 9° C. within 30 h. The initially liquid product was present for the most part in solidified form at the end of the experiment. Subsequently, the jacket temperature was raised from 13° C. to 25° C. within 10 h. In addition to 70 g of mother liquor and 50 g of sweating fractions, 85 g of molten crystal layer were obtained. This end product had an optical purity of 99.9% ee based on (−)-isopulegol.

Example 2

Dynamic Layer Crystallization of an Isopulegol Melt

A stirred apparatus with a planar bottom cooled by means of a jacket (as described in G. F. Arkenbout, Melt Crystallization Technology, Lancaster/Pa., Technomic Publ. Co., 1995 (ch. 10.4.1)) was initially charged with 1003 g of isopulegol of composition 94.7% (−)-n-isopulegol and 5.3% (+)-n-isopulegol (89.4% ee) with a melting point of 10° C. at a temperature of 12° C. The cooling jacket of the crystallizer bottom was cooled to −14° C. over the course of 2 h. In the course of this, a 12 mm-thick crystal layer with a weight of 124 g formed. Subsequently, the apparatus was turned through 180° and the jacket temperature was raised from 8° C. to 13° C. within 10 h. This afforded 52 g of sweating fractions and 124 g of molten crystal layer. This end product had an optical purity of 99% based on (−)-n-isopulegol.

Example 3

Suspension Crystallization of an Isopulegol Melt

A 1 l stirred crystallizer (as described in Arkenbout, ch. 10.4.2) was initially charged with 860 g of an isopulegol isomer mixture having an optical purity based on (−)-n-isopulegol of 95.2% (90.4% ee) as a melt. The melting point of the mixture was approx 10° C. The stirrer used was a close-clearance helical stirrer. In situ seeding of the melt was achieved by brief cooling down to 3° C. and subsequent heating to 9° C. Subsequently, the apparatus was cooled to 7° C. with stirring within 1.5 h, This established a solids content of the suspension of approx. 35% by weight. From this suspension, a sample was taken and freed of adhering mother solution by centrifugation. After centrifuging for one minute, the crystals had a purity of 99% ee based on (−)-n-isopulegol, and of 99.4% after centrifuging for five minutes.

Comparative Example 1

Solution Crystallization of Menthol

In a 1 l stirred crystallizer, 560 g of a menthol isomer mixture (80% ee, purity based on (−)-menthol: 90%) were dissolved in 240 g of acetone. The saturation temperature of the mixture was 5.8° C. After cooling to 5.7° C., the supersaturated solution was seeded with 14 g of seed crystals of pure (−)-menthol and cooled further at a rate of from 0.5 to 1 K/h. On attainment of a temperature of −6.9° C. and a solids content of 22.4% by weight in the suspension, a sample was taken and freed of adhering mother solution by centrifugation. The crystals had a purity of 98.2% (96.4% ee).

Comparative Example 2

Melt Crystallization of Menthol

A jacketed glass tube as a crystallizer was initially charged with 324 g of menthol of composition 95% (−)-menthol and 5% (+)-menthol (90% ee). The melting point of the mixture was 38° C. The crystallizer was cooled from 38.4° C. to 37.4°

C. over the course of 15 h. The initially liquid product was present almost completely in solidified form at the end of the experiment. Subsequently, the jacket temperature was raised from 38° C. to 39° C. within 5 h. This afforded two sweating fractions (51 g and 198 g) and 75 g of molten crystal layer. An analysis showed that starting solution, the two sweating fractions and the crystal layer had virtually identical ee values around 90%.

The invention claimed is:

1. A process for preparing enriched isopulegol of formula (I)

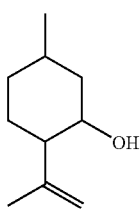

(I)

comprising crystallizing said enriched isopulegol from a melt comprising isopulegol of the formula (I), wherein the crystallization from the melt is in the form of a layer crystallization.

2. A process for preparing enantiomerically and/or diastereomerically enriched n-isopulegol of formula (II)

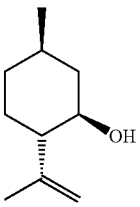

(II)

comprising crystallizing said enantiomerically and/or diastereomerically enriched n-isopulegol from a melt comprising n-isopulegol of formula (II), and optionally further diastereomers of isopulegol, wherein said crystallization from a melt is in the form of a layer crystallization, and wherein the n-isopulegol of formula (II) in said melt has a lower enantiomeric excess than that of the enantiomerically and/or diastereomerically enriched n-isopulegol of formula (II) prepared by said process.

3. The process of claim 1, wherein said melt comprises at least 70% by weight of said isopulegol.

4. The process of claim 2, wherein said melt comprises at least 70% by weight of said n-isopulegol.

5. The process of claim 2, wherein said n-isopulegol in said melt comprises optically active n-isopulegol having a lower enantiomeric excess.

6. The process of claim 1, wherein said crystallization from the melt is performed at a temperature in the range of from −20° C. to 15° C.

7. The process of claim 1, wherein said crystallization from the melt is performed in a static or dynamic manner.

8. The process of claim 1, wherein said crystallization from the melt is performed in the absence of crystallization seeds.

9. The process of claim 2, wherein said n-isopulegol in said melt is present in an enantiomeric excess of at least 75%.

10. The process of claim 1, wherein the chemical purity of the enriched isopulegol is at least 95%.

11. The process of claim 2, wherein said n-isopulegol in said melt is present in an enantiomeric excess of at least 85%.

12. The process of claim 2, wherein the resulting enantiomerically and/or diastereomerically enriched n-isopulegol is enantiomerically enriched L-(−)-n-isopulegol of formula (II*)

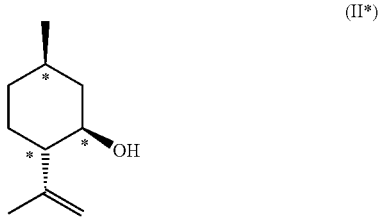

where * in each case denotes an asymmetric carbon atom in the absolute configuration shown.

13. A process for preparing menthol, comprising
a) preparing enantiomerically and/or diastereomerically enriched n-isopulegol of formula (II)

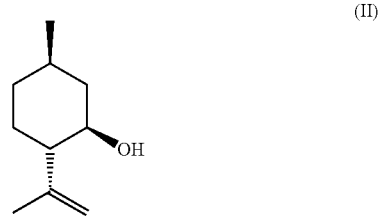

comprising crystallizing said enantiomerically and/or diastereomerically enriched n-isopulegol from a melt comprising n-isopulegol of formula (II), and optionally further diastereomers of isopulegol, wherein said crystallization from a melt is in the form of a layer crystallization; and
b) hydrogenating said enantiomerically and/or diastereomerically enriched n-isopulegol obtained in a).

14. The process of claim 13, wherein said enantiomerically and/or diastereomerically enriched n-isopulegol is L-(−)-n-isopulegol of formula (II*)

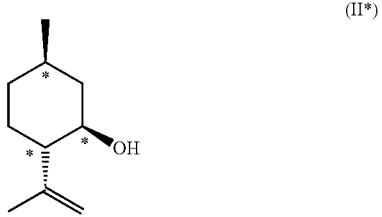

where * in each case denotes an asymmetric carbon atom in the absolute configuration shown.

* * * * *